(12) United States Patent
Wang

(10) Patent No.: US 10,714,211 B2
(45) Date of Patent: Jul. 14, 2020

(54) APPARATUS AND METHOD FOR IMPROVING CHEMICAL PROCESS EFFICIENCY AND PROMOTING SHARING OF CHEMISTRY INFORMATION

(71) Applicant: CHANGZHOU SANTAI TECHNOLOGY CO., LTD., Changzhou, Jiangsu (CN)

(72) Inventor: Ke Wang, Jiangsu (CN)

(73) Assignee: CHANGZHOU SANTAI TECHNOLOGY CO., LTD., Changzhou (CN)

( * ) Notice: Subject to any disclaimer, the term of this patent is extended or adjusted under 35 U.S.C. 154(b) by 544 days.

(21) Appl. No.: 15/641,195

(22) Filed: Jul. 3, 2017

(65) Prior Publication Data
US 2017/0300666 A1 Oct. 19, 2017

Related U.S. Application Data

(63) Continuation of application No. PCT/CN2016/070119, filed on Jan. 5, 2016.

(30) Foreign Application Priority Data

Jan. 9, 2015 (CN) .......................... 2015 1 0012855

(51) Int. Cl.
*G06F 16/00* (2019.01)
*G16C 20/90* (2019.01)
(Continued)

(52) U.S. Cl.
CPC .............. *G16C 20/90* (2019.02); *G06F 16/95* (2019.01); *G06Q 30/00* (2013.01); *G16C 20/10* (2019.02)

(58) Field of Classification Search
CPC ......... G16C 20/90; G16C 20/10; G06F 16/95; G06Q 30/00
See application file for complete search history.

(56) References Cited

U.S. PATENT DOCUMENTS 7,653,607 B2 * 1/2010 Goldwasser ........... G06Q 30/00
706/29
2002/0049548 A1 * 4/2002 Bunin .................... G06N 5/022
702/32

(Continued)

FOREIGN PATENT DOCUMENTS

| CN | 103055541 A | 4/2013 |
| CN | 103203224 A | 7/2013 |
| CN | 104504152 A | 4/2015 |

OTHER PUBLICATIONS

International Search Report of PCT Patent Application No. PCT/CN2016/070119 dated Mar. 31, 2016.

*Primary Examiner* — Jared M Bibbee

(57) ABSTRACT

Apparatus and method for improving chemical process efficiency and promoting sharing of chemistry information for guiding and encouraging scientific researchers and institutions to develop and share more efficient chemical processes. Technical solution comprises: by means of execution and assessment analysis of relevant chemical processes of target compound or target compound system and provision of application program and website having social and electronic transaction functions installed on mobile device for scientific researchers on basis of Internet technology, sharing, transaction and assessment of relevant chemical processes of and chemistry information about compound can be disclosed are implemented, and users are guided and encouraged to share chemistry information and experience via electronic transaction system, developing more efficient chemical processes, reducing resource waste, promoting (Continued)

research and development efficiency, improving research and development efficiency of unknown innovative chemical processes and compounds.

13 Claims, 8 Drawing Sheets

(51) Int. Cl.
*G06F 16/95* (2019.01)
*G06Q 30/00* (2012.01)
*G16C 20/10* (2019.01)

(56) References Cited

U.S. PATENT DOCUMENTS

| | | | |
|---|---|---|---|
| 2006/0277201 A1* | 12/2006 | Dorsett, Jr. | G16C 20/10 |
| 2007/0050092 A1* | 3/2007 | Kenyon | G16B 35/00 |
| | | | 700/266 |
| 2007/0203951 A1* | 8/2007 | Dorsett, Jr. | G06F 16/289 |
| 2007/0214101 A1* | 9/2007 | Wang | G16C 20/60 |
| | | | 706/45 |
| 2008/0015837 A1* | 1/2008 | Smith | G16C 20/10 |
| | | | 703/12 |
| 2008/0126425 A1* | 5/2008 | Cardin | G06Q 10/087 |
| 2014/0282106 A1* | 9/2014 | Smith | G06F 16/176 |
| | | | 715/753 |

* cited by examiner

Query and trade analysis module
114

Matching unit 1141

Transaction unit 1142

Analysis unit 1143

FIG. 1B

APPARATUS AND METHOD FOR IMPROVING CHEMICAL PROCESS EFFICIENCY AND PROMOTING SHARING OF CHEMISTRY INFORMATION

CROSS-REFERENCES TO RELATED APPLICATIONS

This application is a continuation application of PCT Patent Application No. PCT/CN2016/070119, filed on Jan. 5, 2016, which claims priority to Chinese Patent Application No. 201510012855.0, filed on Jan. 9, 2015, the content of all of which is incorporated herein by reference.

FIELD OF THE INVENTION

The present application relates to the field of an apparatus and method of chemical process information related, in particular to an apparatus and method for improving chemical process efficiency and promoting sharing of chemistry information.

BACKGROUND

Currently in the field of chemistry, when a scientific researcher/chemist wants to synthesize a target compound, he will first search a plurality of literatures and patents data including two major chemical databases of SciFinder and Reaxys, to obtain chemistry information of relevant compounds, and based on these information including the literatures and patents information, designing and optimizing a synthetic route of the target compound, as well as obtaining a supply information on a plurality of raw material compounds such as a starting compound and else.

After the target compound being synthesized, generally, it is able to obtain the target compound in certain purity by a plurality of separation and purification methods including chromatography, crystallization/re-crystallization and else. Wherein, most (80-90%) of the synthesized organic compounds may be prepared, separated and purified by a flash chromatography technology after a plurality of appropriate post-reaction processing treatments. The flash chromatography technology has also become a dominant technology in a contemporary liquid chromatography field.

The SciFinder is an online database published by Chemical Abstract Service (CAS) of American Chemical Society (ACS), In addition to querying a daily updated CA data up to 1907, it further provides a structure based search function to researchers. It is the largest and most comprehensive database for chemistry and related scientific information in the world. With its largest scientific data and powerful search function, researchers will be able to follow the latest scientific development and identify the best research direction and achieve optimized resource available. According to statistics, more than 95% of the researchers around the world have highly praised SciFinder, acknowledging that it has inspired and accelerated their research.

While the Reaxys database is published by Elsevier Co., which is a database with rich chemistry data and information, it is an online solution for assisting chemical research and development, and a R&D tool for optimizing chemical synthetic routes. The Reaxys has integrated the database of CrossFire, and has covered comprehensively a plenty of experimental verified information in organic chemistry, metal organic chemistry and inorganic chemistry.

However, the synthetic routes provided by the existing chemistry databases are merely a plurality of data lists based on literatures and patents information, a chemist has to execute screening, feasibility analyzing and route optimizing based on his own theoretical knowledge and experience, while he also has to cooperate with other personnel including a purchaser to execute a screening and determination on a plurality of suppliers for raw material compound, before integrating a plurality of various factors to determine a final feasible synthetic route. However, during an executing process of the determined final synthetic route, often a plurality of unexpected chemical problems and difficulties may rise, while the researcher may find it difficult to communicate with a provider of the referenced literature or patent information on the synthetic route, causing a waste of time and resource, and even a failure of the synthetic route. The existing chemistry information database lacks of a verification and assessment to the provided information, including literature information, patent information, supply information of raw material compounds and else, it also lacks of an update to the existing information, as well as an interaction between the information provider and user.

The prior art may provide a search and trade for a chemical product and chemistry information, may also carry out a relevant chemical process of the target compound or the target compound system. However, when a current chemical device or apparatus is executing a relevant chemical process of the target compound or the target compound system, on one hand, the user can not obtain directly an existing chemical process through the existing chemical device or apparatus, and perform automatically therein, on the other hand, after the user has performed the relevant chemical processes on the target compound or the target compound system, the existing chemical device or apparatus can not make a quantized efficiency comparison and analysis of the currently performed process against the existing processes (if there are any), thus, it is impossible to guide or drive a user to use and/or develop a more efficient chemical process, thus causing a waste of the resources for R&D.

Furthermore, a search and trade platform for chemical products and chemistry information in the prior art lacks of an efficient mechanism to guide and drive the user to publish, verify and evaluate the chemistry information, thus there is no way to decide if the recorded chemistry information was practical and efficient.

Taking the liquid chromatography technology as an example, currently being widely used in the field of synthetic chemistry, the flash chromatography belongs to one of the liquid chromatography technology which was first proposed and improved by W. Clark Still of Columbia University in 1978. Compared to a traditional liquid chromatography separation technology, the flash chromatography technology uses a silica gel packed column with a smaller particle size, to make an efficient separation and purification of the target compound under a certain pressure. Using the chromatographic techniques to separate and purify the target compound is a basic technique that every chemist in the organic synthetic field must master and use daily. Generally, it is possible to use a plurality of columns with different construction materials to manually pack a chromatographic column for separation and purification, or use an automatic liquid chromatography system to separate and purify the compound. Currently a plurality of products based on the flash chromatography technology has been widely applied in the market. With a development of hardware and software technologies, a modern flash chromatography system has been more and more automatic, once a plurality of separation and purification methods have been developed, a user may achieve the separation and purification of the target compound with a simple operation.

However, although the existing liquid chromatography separation technology and the instruments thereof have a good level of automation, the user still have to master a basic chromatographic knowledge and achieve a specialized training. Furthermore, even when a separation method for a specific target compound system was already developed, since there is no system or platform providing a sharing and searching work for the separation method, each time, the user still has to perform a series of experiments to determine a plurality of basic factors of target compound system for separation and purification, such as a solvent system, a Rf value and a gradient, etc., which results in a plurality of repeated thus wasted efforts and valuable research resources.

Further, separation and purification method of a target compound is an integral part of the synthetic process of the target compound, in the prior art, it is impossible to provide combined information regarding the synthetic information and separation and purification information of the target compound, while a chemist has to use different products and services to carry out/complete a synthesis of the target compound before separation and purification, which results in an inefficient use of resources, and thus hinders an advancement of scientific research, as well as improvement of production efficiency.

Furthermore, in prior art, the separation and purification techniques, including the liquid chromatography technology, are isolated from a synthesis process of a compound, the researchers lack of any efficient tools to evaluate the efficiency of the separation and purification method, that is, after a successful separation and purification of a target compound, it is impossible for a researcher to know whether there is a more efficient separation and purification method exist or not, and it lacks of an effective analysis to the efficiency of the separation and purification executed this time, so as to develop a more efficient separation and purification method. Especially in a field of research and development, the technology system in the prior art lacks of a mechanism to guide and drive the scientific researchers to develop and use a more efficient separation and purification technology, causing a waste of resources and a low efficiency of scientific researches.

Therefore, the prior art has yet to be developed.

BRIEF SUMMARY OF THE DISCLOSURE

The following description provides a brief overview of one or more aspects to provide a basic understanding of these aspects. This overview is not an exhaustive overview of all the intended aspects, and it is neither intended to identify a plurality of critical or decisive elements in all respects nor to attempt to define a range of any or all aspects. A sole purpose thereof is providing some concepts of one or more aspects in a simplified form, acting as a prologue of a more detailed description given later.

According to the above described defects, the purpose provided in the present application is providing an apparatus and method capable of improving chemical process efficiency and promoting sharing of chemistry information capable of guiding and driving a plurality of scientific researchers and institutions to develop and share more efficient and optimized chemical processes, in order to solve the problems in the prior art that, causing a waste of resources, while hindering an efficiency of research and develop. Especially, the present application may promote the efficiency of researching and developing an unknown innovative chemical process and compound.

In order to achieve the above mentioned goals, the technical solution provided in the present application to solve the technical problem is as follows:

The present application discloses an apparatus for improving an efficiency of chemical processes and promoting sharing of chemistry information, applied to obtaining and querying characteristic information and chemistry information of the target compound or the target compound system, as well as generating and/or executing a chemical process of the target compound or the target compound system, the said apparatus comprises an execution module, a knowledge base module, a control module and a query and trade analysis module, wherein the execution module, applied to generating and/or executing a chemical process designed by a user or obtained through an electronic transaction, of a target compound or the target compound system;

the knowledge base module, applied to storing the chemistry information of the target compound and/or the target compound system, each type of the chemical process of each target compound and/or each target compound system has an assessed efficiency value, the assessed efficiency value is a reference basis for a chemical process transaction;

the control module, applied to communicating and controlling the execution module, the knowledge base module, and the query and trade analysis module;

the query and trade analysis module, further includes a matching unit, a transaction unit, and an analysis unit, wherein:

the matching unit, applied to searching the knowledge base module of the apparatus, a plurality of other knowledge base modules connected into a network, or a remote central database server for matched chemistry information of the target compound and/or the target compound system through obtained characteristic information of the target compound and/or the target compound system;

the transaction unit, applied to obtaining the matched chemistry information of the target compound and/or the target compound system through electronic transaction, initiated by the user;

the analysis unit, applied to executing an assessment and analysis to the efficiency of the executed chemical process after executing the chemical process which is either designed by the user or obtained through electronic transaction.

An embodiment according to the apparatus for improving chemical process efficiency and promoting sharing of chemistry information provided in the present application, wherein, the same type of chemical process of the same target compound and/or the target compound system is prioritized based on its assessed efficiency values in the knowledge base module, and only the chemical processes of the target compounds and/or the target compound system with the highest assessed efficiency values may be traded.

An embodiment according to the apparatus for improving chemical process efficiency and promoting sharing of chemistry information provided in the present application, wherein, the control module directs the query and trade analysis module to receive the characteristic information of the target compound or the target compound system, and search for the matched chemistry information of the target compound or the target compound system in the knowledge base module of the apparatus, and in the knowledge base module of other devices and/or the remote central database server connected into the internet through the knowledge base module of the apparatus, followed by delivering the retrieved matched chemical processes of the target compound or the target compound system to the execution module to execute the chemical process of the target compound or the target compound system.

An embodiment according to the apparatus for improving chemical process efficiency and promoting sharing of chemistry information provided in the present application, wherein the analysis unit will evaluate accordingly the efficiency of the user designed chemical process performed this time after the user designed chemical process is executed, and generates an analysis report based on a comparison result of the efficiency value between the user designed chemical process performed this time and the matched chemical process stored in the knowledge base, if the matching unit has retrieved a matched chemical process information of the target compound and/or the target compound system, while the execution module is still executing the user designed chemical process according to the user's selection, followed by a plurality of corresponding operations executed by the control module.

An embodiment according to the apparatus for improving chemical process efficiency and promoting sharing of chemistry information provided in the present application, wherein the user updates and/or improves the matched chemical processes obtained, after the transaction unit obtains the matched chemical process through electronic transaction according to the user's request, followed by being executed by the execution module, if the matching unit has retrieved the chemical process information matching the target compound and/or the target compound system; and after finishing executing the said chemical processes updated or improved by the user, the analysis unit will evaluate the efficiency of the user updated or improved chemical process performed this time accordingly, and perform a comparison of the efficiency value based on the user updated and/or improved chemical process performed this time with the matched efficiency value of the chemical process stored in the knowledge base before generating a analysis report, followed by a plurality of according operations performed by the control module.

An embodiment according to the apparatus for improving chemical process efficiency and promoting sharing of chemistry information provided in the present application, wherein the execution unit performs the user designed chemical process, and the analysis unit performs assessment and analysis on the efficiency of the executed chemical process, before a plurality of according operations being performed by the control module, if the matching unit has not retrieved any chemical process information matching the target compound and/or the target compound system.

An embodiment according to the apparatus for improving chemical process efficiency and promoting sharing of chemistry information provided in the present application, wherein the according operation of the control module is: the control module generates one-step synthetic route information of the target compound according to the characteristic information of target compound system, the one-step synthetic route information is then correlated to the chemical process of the target compound or the target compound system generated by the execution module and the supply information of the obtained target compound, before being saved to the knowledge base module, as well as prompting and guiding the user to upload the newly added or updated and/or improved chemical process of the target compound or the target compound system to the knowledge base.

An embodiment according to the apparatus for improving chemical process efficiency and promoting sharing of chemistry information provided in the present application, wherein the query and trade analysis module is running in a computer chip of the apparatus or in an independent terminal device.

An embodiment according to the apparatus for improving chemical process efficiency and promoting sharing of chemistry information provided in the present application, wherein the execution module comprises a separation and purification unit or a chemical synthetic reaction unit, wherein the separation and purification unit includes a chromatographic apparatus, a crystallization/re-crystallization apparatus, and a rectifying apparatus.

An embodiment according to the apparatus for improving chemical process efficiency and promoting sharing of chemistry information provided in the present application, wherein the chemistry information of the target compound or the target compound system stored in the knowledge base module includes synthetic route information, separation and purification method information and supply information of the target compound, while the knowledge base module interacts with the external central database server or the knowledge base modules of other apparatuses for data obtaining and updating.

The present application further discloses a method for improving chemical process efficiency and promoting sharing of chemistry information, comprising:

receiving the characteristic information of the target compound or the target compound system;

searching for the matched chemistry information of the target compound and/or the target compound system in the knowledge base of the apparatus, in the knowledge base of other apparatuses, and in the remote central database server locating at a far end of the Internet, according to the characteristic information of the target compound or the target compound system;

obtaining the matched chemistry information matching the target compound and/or the target compound system through electronic transaction upon a user's request, wherein each type of the chemical process of each target compound or target compound system has an assessed efficiency value, and the assessed efficiency value is a reference basis for the chemical process transaction;

executing the user designed chemical process, or executing directly the chemical process obtained through the electronic transaction, or executing the user updated or improved chemical process obtained through the electronic transaction, followed by executing assessments to the efficiency of the executed chemical process after the execution finished;

based on an analysis and comparison result between the assessed efficiency value of the chemical process executed this time with the efficiency value of the matched chemical process stored in the knowledge base, prompting and guiding the user to add or update the chemistry information of the target compound or the target compound system stored in the knowledge base.

An embodiment according to the method for improving chemical process efficiency and promoting sharing of chemistry information provided in the present application, a same type of chemical process of the same target compound or target compound system stored in the knowledge base is prioritized based on its assessed efficiency value, only the chemical process of the target compound and/or the target compound system with a highest assessed efficiency value may be traded.

An embodiment according to the method for improving chemical process efficiency and promoting sharing of chemistry information provided in the present application, wherein the efficiency of the user designed chemical process performed this time is assessed after executing the user designed chemical process, if a chemical process information matching the target compound or the target compound system is retrieved, while the system is still executing the user designed chemical process; and the user is prompted and guided to perform an update operation to the knowledge base, based on an analysis and comparison result of the assessed efficiency value of the user designed chemical process performed this time higher than that of the matched chemical process stored in the knowledge base.

An embodiment according to the method for improving chemical process efficiency and promoting sharing of chemistry information provided in the present application, wherein the user updates and/or improves the matched chemical processes after the matched chemical process is obtained through an electronic transaction according to the user's request, if the chemical process information matching the target compound and/or the target compound system has been retrieved; the user then directs the execution module to execute the updated and/or improved chemical process, and after finishing executing the chemical processes updated or improved by the user, the efficiency of the user updated or improved chemical process performed this time will be evaluated, and based on an analysis and comparison result of the assessed efficiency value of the user updated and/or improved chemical process performed this time higher than the assessed efficiency value matching the chemical process stored in the knowledge base, the user will be prompted and guided to perform an update operation to the knowledge base.

An embodiment according to the method for improving chemical process efficiency and promoting sharing of chemistry information provided in the present application, wherein the user designed chemical process will be executed, if any chemical process information matching the target compound and/or the target compound system are not retrieved, and a plurality of adding operations to the knowledge base will be performed after assessing and analyzing the efficiency of the executed chemical process.

An embodiment according to the method for improving chemical process efficiency and promoting sharing of chemistry information provided in the present application, wherein the chemistry information of the target compound or the target compound system stored in the knowledge base includes the synthetic route information, the separation and purification method information and the supply information of the target compound, the knowledge base interacts with the external central database server or the knowledge base in other apparatuses capable of data obtaining and updating.

Comparing to the prior art, the present application has a plurality of benefits as follows: through executing, evaluating and analyzing the related chemical processes of the target compound or the target compound system, and based on the Internet technology, the present application provides a scientific researcher an App program and a website installed in a mobile device owning a social function and an electronic transaction function, thus achieving a sharing, trading and assessing of the chemistry information of the compound being able to be disclosed (wherein the chemistry information includes the chemical process), guides and drives the user to share the chemistry information and experience through the electronic transaction system, so as to develop a more efficient chemical process. It may reduce resources waste, promote a R&D efficiency, especially, the present application may promote the efficiency of researching and developing an unknown innovative chemical process and compound thereof.

In more details, a plurality of technical keys and innovative aspects of the present application are:

the present application uses the Internet technology and establishes a transaction and sharing platform for chemical products and chemistry information through an e-commerce website owning social and transaction functions and an App program installed in the mobile terminal device, it also combines a kind of chemical device or apparatus to obtain, verify, improve and update the current chemistry information of the target compound or the target compound system through executing the related chemical processes of the target compound or the target compound system. Through the transaction and sharing platform and the chemical device or apparatus provided in the present application, a user may download, execute and verify the existing related chemical processes of the target compound or the target compound system, may publish a not yet exist chemical process or a chemical process with a higher efficiency than the related chemistry information of the current target compound or target compound system, and make a relative transaction. The present application may achieve an obtaining, executing verification and updating of the chemistry information of the target compound or the target compound system, may also guide and drive the user to develop and use a more efficient chemical process, so as to improve the R&D and production efficiency, reduce the risk of chemical products and chemistry information transactions, and avoid waste of the R&D resources.

BRIEF DESCRIPTION OF THE DRAWINGS

FIG. 1B illustrates a refined schematic diagram of a query and trade analysis module shown in the FIG. 1A.

Figure 1A:
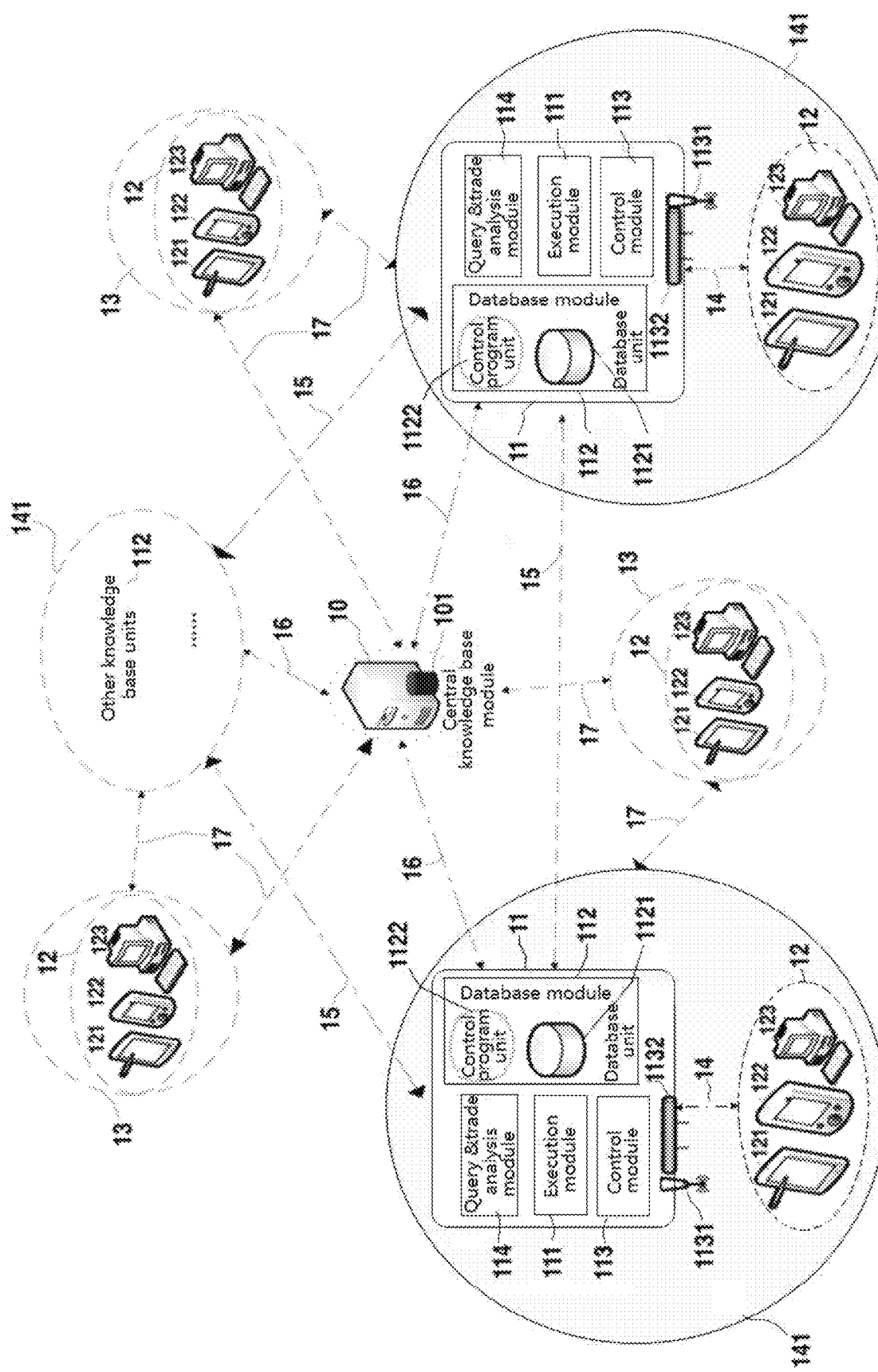
FIG. 1A illustrates a system architecture diagram of a preferred embodiment of an apparatus for improving chemical process efficiency and promoting chemistry information sharing as provided in the present application.

Wherein:

Organization: refers to an enterprise, a university, a research institute and other statutory body or group.

User: refers to a scientific researcher.

Target compound: refers to a compound or a pure substance that the user needs to synthesize and/or separate & purify.

Starting compound: in the present application, it is referred specially to one or more raw material compounds applied to directly one-step synthesizing the target compound.

Target compound system: refers to a mixture comprising the target compound and/or the starting compound and/or the impurity compound.

Chemical process: comprises but not limited to: a synthetic process and information of the target compound, a separation and purification process and information of the target compound or the target compound system.

Chemistry information of a compound: refers to a comprehensive knowledge and information comprising the related chemical process, supply information, and other physical and chemical properties relative to the compound.

Knowledge base: refers to a database storing the chemistry information of the compound.

Characteristic information of a compound: refers to information that can uniquely characterize a compound, including but not limited to: molecular structure information of the compound, naming information of the compound, a unique CAS code or MDL code of the compound.

Characteristic information of a target compound system: refers to information that may uniquely represent target compound system including the molecular structure information of the starting compound or the CAS code or the MDL code, the molecular structure information of the target compound or the CAS code or the MDL code, and/or the molecular structure information of the impurity compound.

02: a general name of all the knowledge bases, including a central knowledge base module 101, a centered knowledge base module 102 and a knowledge base module 112 in the apparatus.

10: a cluster of central database server located in the world wide web, or the Internet.

101: a sharable central knowledge base module located in the network, and running in the cluster of the central database server 10.

102: a centered knowledge base module locating inside the organization.

11: a chemical device or apparatus.

111: an execution module: may execute series of the chemical processes against the target compound or the target compound system based on a received user instruction and/or computer instruction, including but not limited to the synthetic processes and the separation & purification processes.

112: a knowledge base module: including a software and hardware system running in the chemical device or apparatus 11 of the database.

1121: a database unit in the knowledge base module 112.

1122: a control program unit in the knowledge base module 112.

113: a control module in the chemical device or apparatus 11.

1131: a wireless network communication unit.

1132: a wired network communication unit.

114: a query and trade analysis module.

12: a terminal device. Mainly acts as a user interaction interface of the chemical device or apparatus 11, applied to receiving an input of the user information and an information feedback of the chemical device or apparatus 11. As well as acting as a carrier capable of running the mobile terminal App programs, which may perform inquiry, interaction and transaction with the user, an electronic transaction website and the knowledge base 02.

121: a mobile terminal device of smart phone.

122: a mobile terminal device of tablet PC.

123: a computer terminal device, including a laptop computer terminal.

13: a joint name of networks beyond a wireless network range 141 founded by the wireless network communication unit 1131.

14: a wireless or wired network connection, acting as a data communication channel between the terminal device 12 and the control unit in the chemical device or apparatus 11.

141: a wireless communication network owning a limited physical communication range achieved by the wireless network communication unit 1131 in the control module of the chemical device or apparatus 11.

15: a network connection, it is mainly a local area network (LAN) connection, it may also be a wide area network (WAN) connection, which is mainly applied for data communication between different knowledge base modules 112.

16: a WAN connection, mainly applied for the data communication between the knowledge base module 112 and the central knowledge base module 101.

17: a network connection, including a LAN connection and a WAN connection, which is mainly applied for data communication between the terminal device 12 and the chemical device or apparatus 11 and/or a cluster of the central database server 10.

50: an organization.

501: a plurality of database server inside the organization 50, which may be one, or multi.

51: a user terminal, a collection including the user, chemical device or apparatus 11 and the network.

511: a data communication network between the terminal device 12 and the chemical device and apparatus 11.

512: a user inside the organization 50.

52: a specialized network connection inside the organization, applied for the data communication between the chemical device and apparatus 11 inside the organization and the centered knowledge base module.

53: a WAN connection, mainly applied for the data communication between the centered knowledge base module 102 and the central knowledge base module 101.

DETAILED DESCRIPTION OF EMBODIMENTS

The invention provides an apparatus and method for improving chemical process efficiency and promoting sharing of chemistry information provided in the present application. In order to make the purpose, technical solutions and the advantages provided in the present application clearer and more explicit, further detailed descriptions provided in the present application are stated here, referencing to the attached drawings and some embodiments provided in the present application. It should be understood that the detailed embodiments of the invention described here are used to explain the present application only, instead of limiting the present application.

It may better understand the above listed characters and advantages of the present application, after studying a detailed description of the embodiments in the present disclosure with referencing to the following drawings. In the drawings, each component may not necessary be drawn in scale, while the components having a similar relative feature or characteristic may own a same or similar reference number.

Before explaining a device structure and a method process of the present application, a working principle of the present application is stated in detail first.

An efficiency of every chemical process may be characterized after an assessment factor being decided through an evaluation system, the said evaluation system mainly comprises a cost of a chemical process (including but not limited to a raw material cost and a labor cost), a yield rate and a plurality of other factors, the assessment factor decided by the said evaluation system is a specific value, which is characterized as an efficiency value of a chemical process. Among every chemical process according to each target compound or target compound system, only one chemical process having a highest efficiency value may be traded.

When a user is executing the related chemical processes of the target compound or the target compound system with a chemical device or apparatus, first a knowledge base will be searched according to a characteristic information of the target compound or the target compound system, if a matched relative chemical process is retrieved, then the user may choose buying and downloading the specific chemical process before executing directly in the chemical device or apparatus, and may improve the efficiency of the existing process before uploading to the knowledge base to replace the existing process for trading. If the user chooses not to download the specific chemical process, he may then manually set and perform the related chemical process of the target compound or the target compound system by using the chemical device or apparatus, and after finishing executing the chemical process, the user may be prompted and guided after analyzing and comparing the efficiency value of the chemical process executed this time and that of the matched chemical process in the knowledge base: if the efficiency value of the chemical process executed this time is higher than that of the matched chemical process in the knowledge base, the user may then be prompted that he may choose to upload the chemical process executed this time to replace the matched chemical process in the knowledge base for trading; if the efficiency value of the chemical process executed this time is less than that of the matched chemical process in the knowledge base, then the user will be prompted that he should directly buy and download the matched chemical process next time, while the resources may be saved by such an operation will be showed. If there is no matched related chemical process retrieved, the user may upload the related chemical process to the knowledge base for trading after manually setting and executing the related chemical process of the target compound or the target compound system by using a chemical device or apparatus.

The present application may analyze and obtain the one-step synthetic route information of the target compound according to the obtained characteristic information of the target compound system. After the chemical device or apparatus finishes executing the related chemical process of the target compound or the target compound system, potential supply information of the target compound may be generated. That is, the organization in which the user uses the chemical device or apparatus to execute the related chemical process of the target compound or the target compound system may become a potential and certified supplier of the target compound. That is, after the chemical device or apparatus has successfully performed the related chemical process of the target compound or the target compound system, the user's information will be associated to the supply information of the target compound, and after obtaining an authorization from the user, the organization where the user locates will be marked as a certified supplier of the target compound, wherein, the user information further comprises the user's geographic location information.

The apparatus and method of the present application are implemented according to the above-described principle. Referencing to FIG. 1A, which illustrates a system architecture diagram of a preferred embodiment of an apparatus for improving chemical process efficiency and promoting chemistry information sharing as provided in the present application.

The apparatus 11 shown in the FIG. 1A is applied to obtaining and querying characteristic information and chemistry information of the target compound or the target compound system, before generating and/or executing a chemical process of the target compound or the target compound system. The apparatus 11 comprises an execution module 111, a knowledge base module 112, a control module 113 and a query and trade analysis module 114. The apparatus 11 interacts with other apparatuses 11 through a network. In the FIG. 1A, it is further illustrated that at least one chemical device or apparatus 11, a central database server 10 (which comprises a central knowledge base module 101) connected to Internet and at least one terminal device 12 are interacting with each other. The terminal device 12 in the FIG. 1A may query a work state and work result of the chemical device or apparatus through a network connection 17, and may query compound information in the knowledge base module 112 and/or the central knowledge base module 101.

The execution module 111 executes a related chemical process of the target compound or the target compound system based on a work instruction delivered by the control module 113, including but not limited to a separation & purification process and a synthetic process, that is, the execution module 111 comprises a separation & purification unit or a chemical synthetic reaction unit, wherein, the separation & purification unit includes a chromatography apparatus, a crystallization/re-crystallization apparatus, a distillation apparatus and more. The apparatus 11 may download the current chemical processes of the target compound or the target compound system from the knowledge base 02 after being authorized through a method of electronic transaction, followed by executing directly or after adjusting a plurality of related factors, of course, it is also possible to perform manually the related chemical process of the target compound or the target compound system designed by the user.

The apparatus 11 may generate new or updated related chemistry information of the target compound or the target compound system before saving into the knowledge base module 112, after executing the related chemical process of the target compound or the target compound system. Through a network connection 15, different knowledge base modules 112 in different chemical devices or apparatuses 11 may make a plurality of data exchanges, including but not limited to: obtaining new chemistry information, transmitting or updating existing chemistry information.

The knowledge base module 112 further includes a database unit 1121 and a control program unit 1122, wherein, the database unit 1121 is applied to storing chemistry information, which means all chemistry information of the target compound or the target compound system generated by the apparatus itself, and those obtained from an external knowledge base. In a real embodiment, it may comprise a synthetic route information, separation & purification method information and supply information. Each type of chemical process of every target compound or target compound system owns an assessed efficiency value, which is a reference basis for the transaction of the chemical process. A control program unit 1122 is applied to obtaining and updating the chemistry information, as well as communicating and controlling other modules or units (or the control module 113), the execution module 111 and the query and trade analysis module 114. Between the knowledge base modules 112 in each apparatus 11 connected to the network, it is possible to make a data exchange and a data update through the network connection 15. The knowledge base modules 112 in the apparatus 11 connecting to the network may further make a data communication through a WAN 16 with the central knowledge base module 101 in the central database server 10 connected to Internet, including but not limited to an update and synchronization between the knowledge base modules 112 and the central knowledge base module 101, wherein the central knowledge base module 101 has all the chemistry information recorded and uploaded of the known compounds stored. Additionally, the apparatus 11 may further make data communication after installing the network connection 17 with the central knowledge base module 101 through the terminal device 12 connected to the Internet, including but not limited to an inquiry of the chemistry information, an update and synchronization of both the knowledge base modules 112 and the central knowledge base module 101.

The control module 113 further has a network communication unit, furthermore, it may include a wireless network communication unit 1131 and a wired network communication unit 1132, applied to communicating and controlling the terminal devices 12 and the execution module 111, the knowledge base module 112 and the query and trade analysis module 114. When the user is in a wireless communication network 141 founded by the wireless network communication unit 1131, it is possible to use the mobile terminal device 121 and/or 122 to found a wireless network connection 14 to the chemical device or apparatus 11, as well as operating and controlling the apparatus 11 through the control module 113. While the user is beyond the wireless communication network 141, it is possible to setup the network connection 17 to the chemical device or apparatus 11 through the terminal device 12, and query the work status and work result of the apparatus 11 through the control module 113, as well as querying and updating the chemistry information of the compound in the knowledge base module 112 and/or the central knowledge base module 101. The control module 113 instructs the query and trade analysis module 114 to receive the characteristic information of the target compound or the target compound system, searches for and obtains the supply information of the matched chemical process and compound of the target compound or the target compound system in the knowledge base module 112, followed by delivering the searched results to the execution module 111 to perform the chemical processes of the target compound or the target compound system.

The query and trade analysis module 114 is running in a computer chip in the apparatus or in an independent terminal device, whose detailed structure is referencing to the FIG. 1B, wherein the module 114 comprises a matching unit 1141, a transaction unit 1142 and an analysis unit 1143.

Through the obtained characteristic information of the target compound or the target compound system, the matching unit 1141 searches the knowledge base module 112 of the apparatus, other knowledge base modules connected to the network or the central knowledge base module 101 in the central database server 10 connected to an other end of the Internet for the matched chemistry information of the target compound or the target compound system, for example, after connecting to different apparatuses, it may search for all related chemistry information of the target compound, including a separation process, a synthetic process, a supply information, a plurality of physical properties, and a plurality of related applications.

A matching result may have two possibilities: one is having a matched result, and the other is having no matched result. In a case of having no matched result, the execution module 111 will perform the user designed chemical process, followed by the analysis unit 1143 evaluating the efficiency of the executed chemical process, before transmitting to the control module 113 for according operations.

The transaction unit 1142 obtains the matched chemistry information of the target compound or the target compound system through electronic transaction according to the user's inquiry.

In a case of having a matched result, the execution module 111 may have two ways for implementation, one is obtaining the matched chemistry information of the target compound or the target compound system through electronic transaction according to the user's inquiry through the transaction unit 1142, before transmitting the obtained chemical process to the execution module 111 to perform the chemical process. Furthermore, the user may make a self-adjustment after obtaining the matched information of the chemical process, and may execute the self-adjusted chemical process, before transmitting to the analysis unit 1143 to evaluate the efficiency of the adjusted chemical process, before generating an analysis report, followed by making according operations by the control module.

Another way is that, the execution module still performs the user designed chemical process according to the user's selection; the analysis unit 1143 makes an assessment on the efficiency of the user designed chemical process accordingly, and makes an analysis and comparison of the efficiency values of the matched chemical processes stored in the knowledge base and the efficiency value of the user designed chemical process, followed by generating the analysis report before executing the according operations by the control module.

In order to ensure that the chemical process being able to trade stored in the knowledge base is the one currently having the highest efficiency value (as what has been stated before, the knowledge base may store all kinds of chemical process protocols according to each case, but only the one with the highest efficiency value may be traded), thus, after the analysis unit 1143 has evaluated the efficiency value of the adjusted chemical process either designed by the user or downloaded through the electronic transaction, it will be compared to the efficiency values of the original chemical processes already saved in the knowledge base 02, if the efficiency value of the chemical process performed is lower than that of the chemical processes stored in the knowledge base 02, then the system will prompt and suggest the user to choose an existing chemical process in the knowledge base 02 to execute directly; if the efficiency value of the chemical process performed is higher than that of the chemical processes stored in the knowledge base 02, then the system will prompt and guide the user to upload the new chemical process to replace the original chemical process saved in the knowledge base 02. A specific implementation of such a replacement is: the control module 113 generates the synthetic route information of the target compound according to the characteristic information of the target compound system, and saves to the knowledge base module 112 after correlating with the chemical process of the target compound or the target compound system generated by the execution module 111, and the obtained supply information of the target compound, followed by the knowledge base module 112 transmitting automatically the updated information to other knowledge base modules 112 online and the central database server 10 through the network connection.

Figure 6:
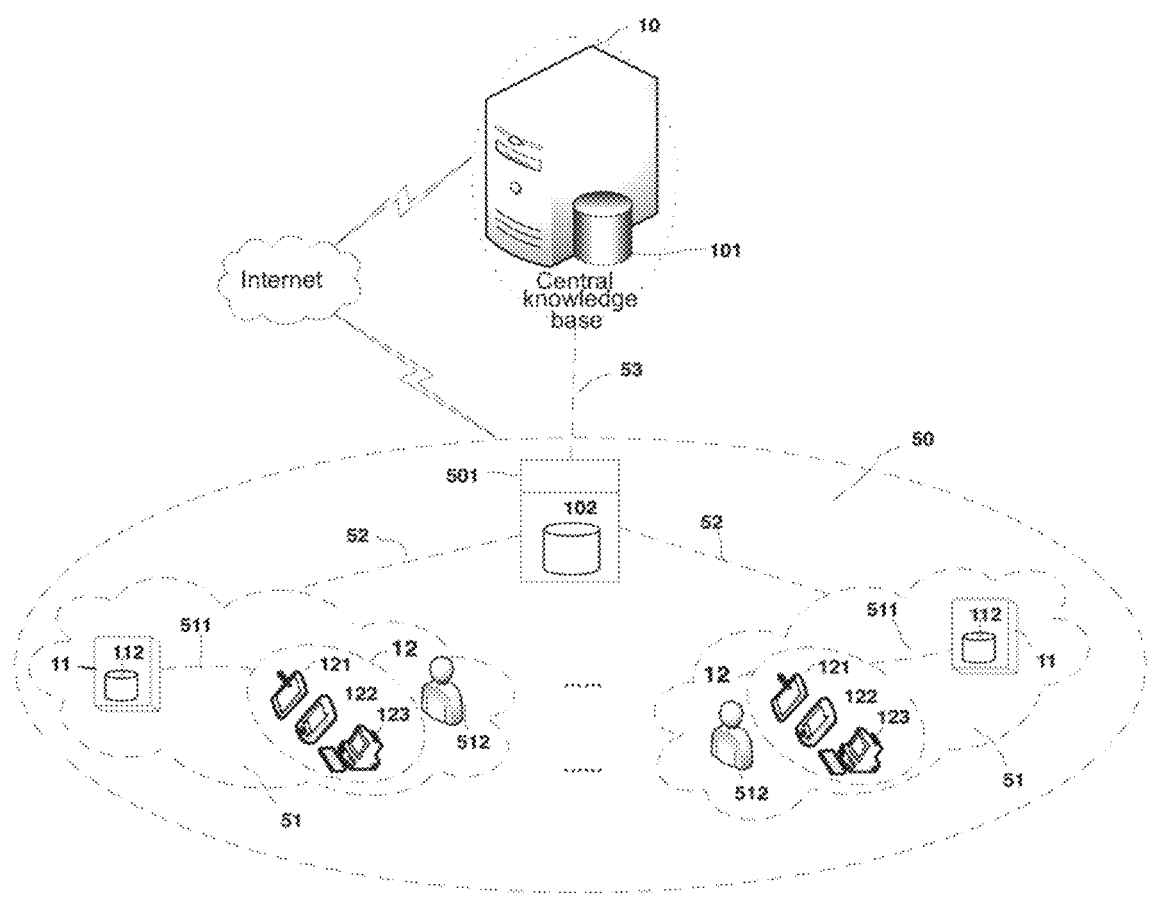
FIG. 6 illustrates a system configuration diagram of a variation of the present application.

FIG. 6 describes a variation of the apparatus of the present application. Inside the organization 50, there are one or a plurality of central database servers 501 installed, the knowledge base module 112 in the one or the plurality of chemical devices or apparatuses 11 inside the organization each makes a data exchange with the centered knowledge base module 102 in the central database server 501 locating at a center of the organization, the centered knowledge base module 102 makes data exchange with the central knowledge base module 101 through an Internet connection 53, to obtain and/or transfer the chemistry information. The knowledge base module 112 in the chemical device or apparatus 11 may achieve a data exchange with the centered knowledge base module 102 through a computer technology of a server/client. The centered knowledge module 102 and the central knowledge base module 101 may also achieve the data exchange through the computer technology of a server/client, therefore an obtaining/updating of the chemistry information is then achieved.

Additionally, other variations of the apparatus such as each software and hardware control module of the query and trade analysis module 114, the control module 113, the knowledge base module 112 and the execution module 111 may be integrated into a high performance embedded hardware and software system, may also be an independent hardware and software system.

The control program unit 1122 in charge of the data exchange of the database unit 1121 may be achieved by installing in the database module 112, or the control module 113.

The software control unit of the execution module 111 may be achieved by installing in the execution module 111, or in the control module 113.

Further, the software control programs in all chemical devices or apparatuses 11 may be integrated in a computer program, to achieve an operation and control to the execution module 111, the database module 112, and the query and trade analysis module 114.

Figure 2:
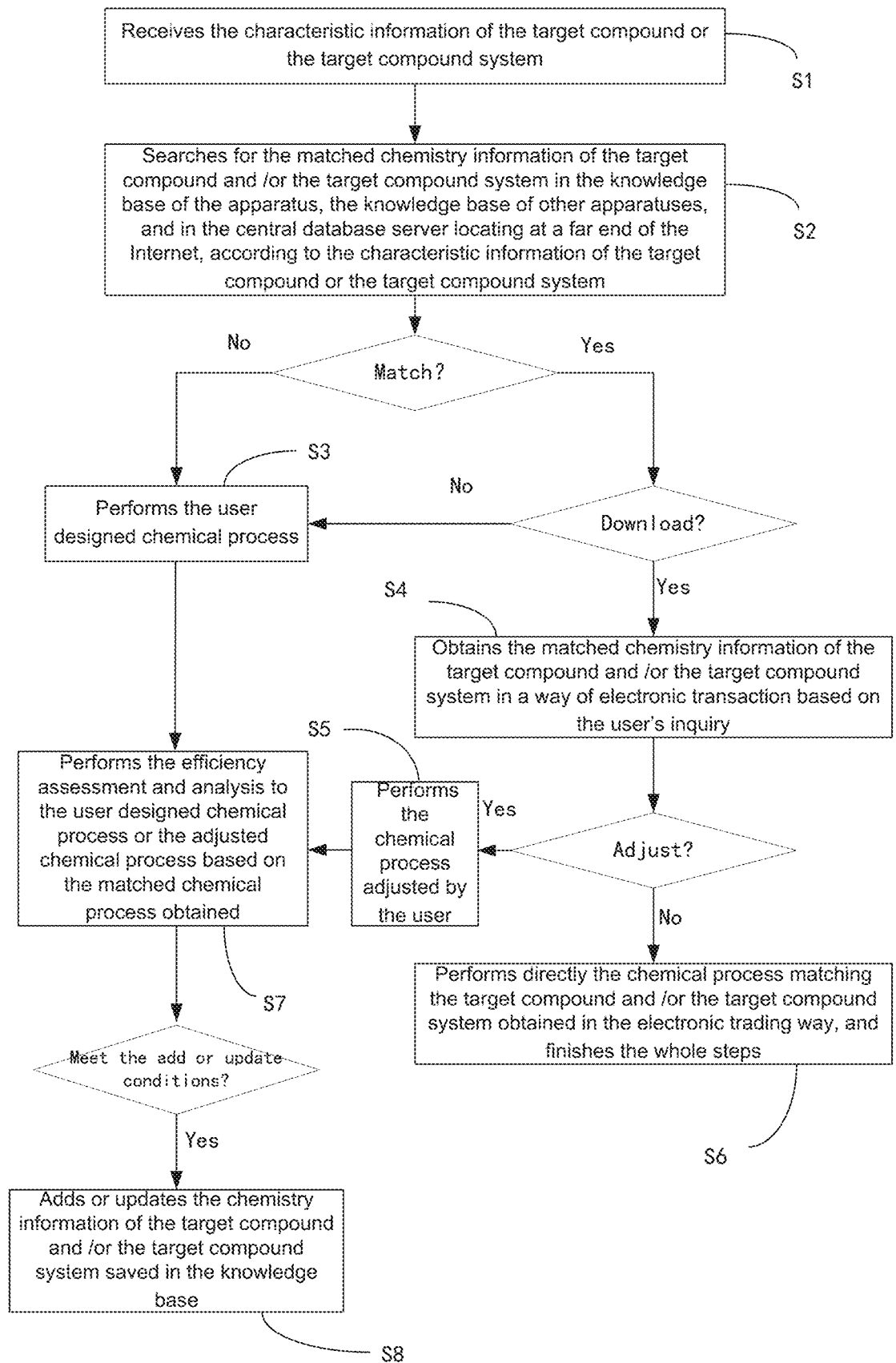
FIG. 2 illustrates a flowchart of a preferred embodiment of a method for improving chemical process efficiency and promoting sharing of chemistry information provided in the present application.

FIG. 2 illustrates a flowchart of a preferred embodiment of a method for improving chemical process efficiency and promoting sharing of chemistry information provided in the present application. A plurality of detailed steps of the method of the present application is as follows:

Step S1: receives the characteristic information of the target compound or the target compound system.

The characteristic information of the target compound system expresses the characteristic information of the starting compound and the target compound and/or the impurity compounds (if there are).

Step S2: searches for the matched chemistry information of the target compound and/or the target compound system in the knowledge base of the apparatus, the knowledge base of other apparatuses, and in the central database server locating at a far end of Internet, according to the characteristic information of the target compound or the target compound system.

Chemistry information of the target compound or the target compound system saved in the knowledge base 02 comprises the chemical processes information and other information including the supply information, specifically, for example, it comprises the synthetic route information, the separation and purification method information and the supply information of the target compound and/or the target compound system, while the knowledge base of the apparatus interacts with the central database server outside or the knowledge base of other apparatuses to obtain and update the data. Wherein each type of the chemical process of each target compound and/or the target compound system has an assessed efficiency value, only the chemical process of the target compound and/or the target compound system owning a high assessed efficiency value may be traded.

If a matched chemical process is retrieved, then it will be further decided if it is needed to download the matched chemical process, if it is needed, then step S4 will be performed, if it is not needed, then step S3 will be performed.

Step S3: performs the user designed chemical process, followed by executing step S7.

Step S4: obtains the matched chemistry information of the target compound and/or the target compound system through electronic transaction upon the user's request.

The electronic transaction mentioned here means a trading and sharing platform for the chemical products and chemistry information, which is founded by an electronic business website owning a social and trading function or an APP program installed in a mobile terminal device. The platform records the user input and/or the user related chemistry information generated by the chemical device or apparatus of the target compound and/or the target compound system. The according chemical process in the chemistry information owns a uniqueness, which means that, the target compound or the target compound system may enumerate (distinguish) the associated chemical processes according to a plurality of conditions including the source and the yield of the target compound, and in each condition, the associated chemical process enumerated may be traded in the trading and sharing platform. Furthermore, for each condition, the user uploaded associated chemical processes may be enumerated, while only one associated chemical process having the highest efficiency evaluated by the evaluation system of the platform may be traded on the trading and sharing platform.

Adjusts the matched chemical process obtained according to the user's requirement, if an adjustment is needed, then step S5 will be performed, if an adjustment is not needed, then step S6 will be performed.

Step S5: performs the chemical process adjusted by the user, then goes to step S7.

Step S6: performs directly the matched chemical process of the target compound and/or the target compound system obtained in the electronic trading way, before finishing the whole steps.

Step S7: performs the efficiency assessment and analysis to the user designed chemical process or the adjusted chemical process based on the matched chemical process obtained.

If the efficiency value of the performed chemical process (brand new or updated) is higher than that of the existing chemical processes stored in the knowledge base 02, goes to step S8, otherwise, the analysis report will prompt the user that he should download and use the existing chemical process to save the related resources, before finishing the whole steps.

This assessment includes but not limited to: an evaluation system for a plurality of supply and use information including a cost of the starting compound, a stock status or an expected date of a customized synthesis, a property of security, a property of stability and more; an evaluation system for a reaction efficiency of each step of the synthetic process in the synthetic route, including but not limited to, a plurality of reaction efficiencies including a temperature, a pressure, a reaction time, a yield, a cost and else; as well as a verification and evaluation system for an authenticity and repeatability of the synthetic route and the one-step synthetic process of all related starting compounds. According to the evaluation system described above, the method provided in the present application decides an optimized synthetic route for the said target compound.

Step S8: adds or updates the chemistry information of the target compound and/or the target compound system saved in the knowledge base 02.

It may be known from the above listed steps that, if the efficiency value of the user designed chemical process is higher than that of the chemical processes currently stored in the knowledge base 02, the system will prompt and guide the user to upload his chemical process having a higher efficiency value, which allows other users need this chemical process to obtain the high efficient chemical process, hereby improves an efficiency of the R&D.

Figure 3A:
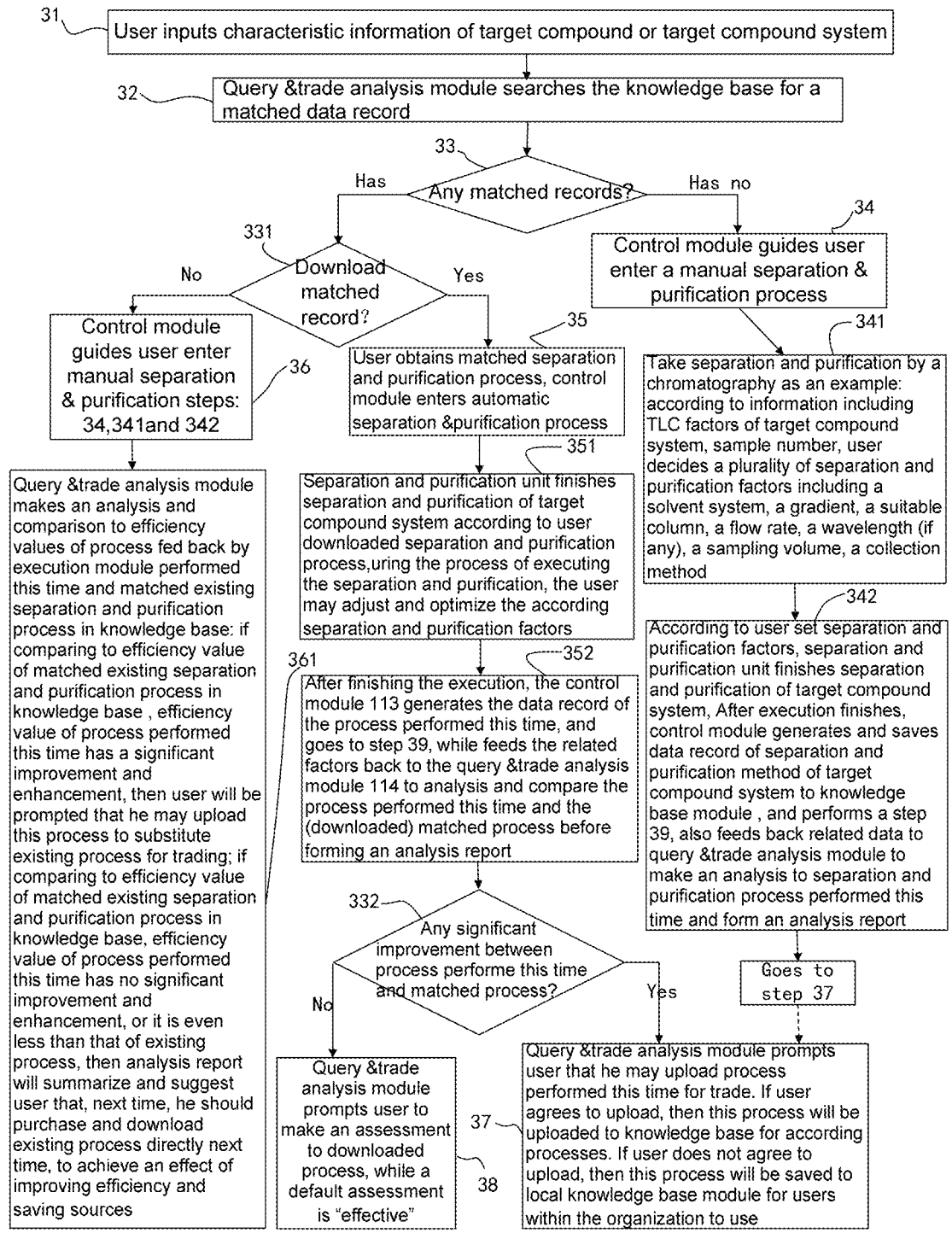
FIGS. 3A and 3B illustrate a flowchart on a method for guiding and driving a user to develop and share more efficient chemical processes through querying, transaction, analysis and verification processes, taking a separation and purification process as an embodiment in the present application.
Figure 3B:
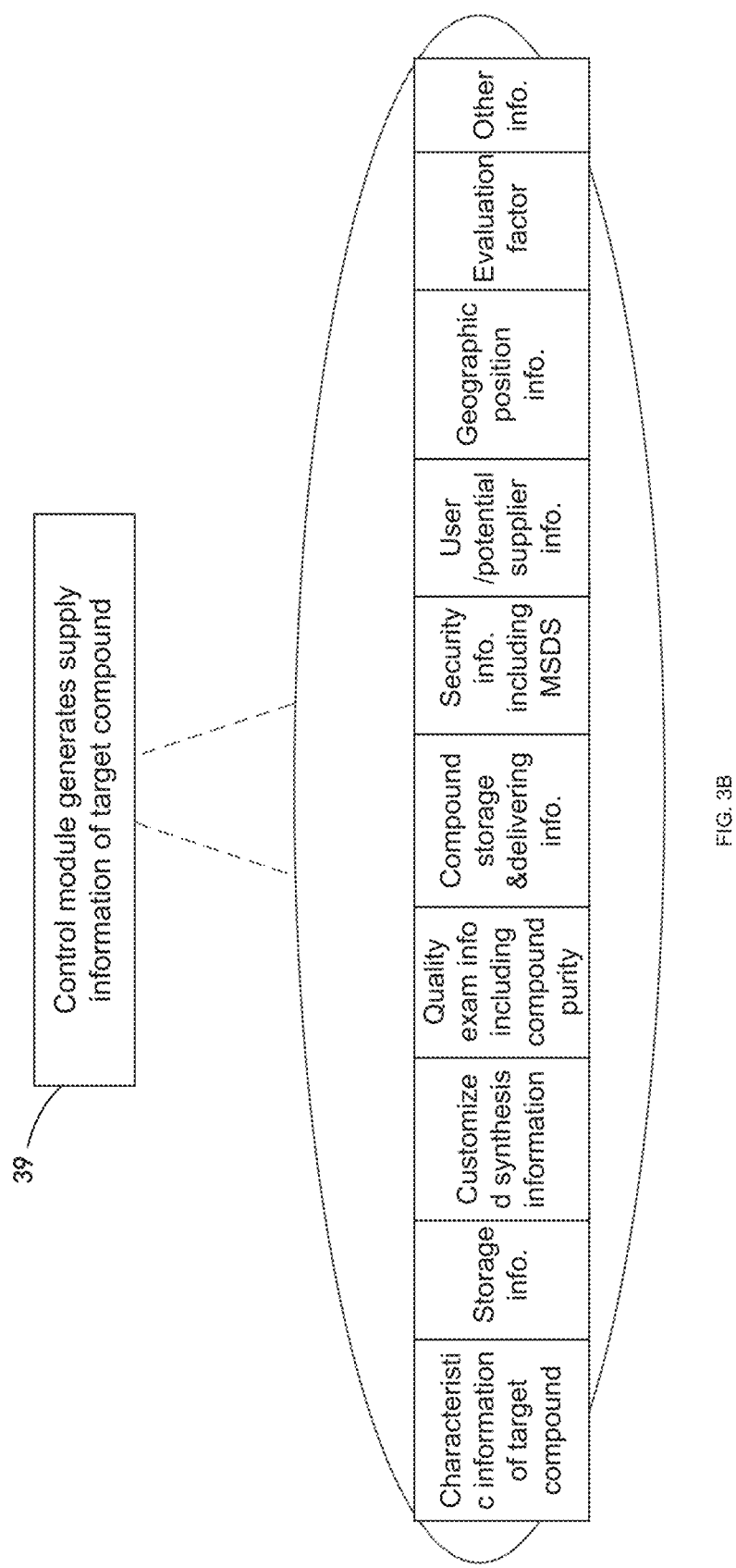

FIG. 3A and FIG. 3B further take the separation and purification as an example, which guides and drives the user to develop and share the method and process of a chemical process with a higher efficiency through querying, transaction, analysis and verification processes, specific steps are as follows, referencing to the devices shown in the FIGS. 1A and 1B.

Step 31: the user inputs the characteristic information of the target compound or the target compound system through the terminal device 12 connecting to the chemical device or apparatus 11 through the network connection 14, and the related information are delivered to the query and trade analysis module 114.

Step 32: the query and trade analysis module 114 searches the knowledge base 02 for a matched data record.

Step 33: feeds back if there is or not a data record matching the target compound or the target compound system. If so, goes to step 331, otherwise, goes to step 34.

Step 34: if there is no matched data record, the control module 113 guides the user to enter a manual separation & purification process.

Step 341: take the separation and purification by a chromatography as an example: the user decides a plurality of basic factors of separating and purifying the target compound system such as a solvent system, a gradient, a suitable column, a flow rate, a wavelength (if any), a sampling volume, a collection method and more through a TLC experiment, according to the characteristic information of the target compound system combing with the chromatography separation basic theory.

Step S342: the execution module (here it is the separation and purification unit) 111 finishes the separation and purification of the target compound system according to the user set separation and purification factors. After the execution, the control module 113 generates and saves the data record of the separation and purification method of the target compound system to the knowledge base module 112, and performs step 39, also feeds the related data back to the query and trade analysis module 114 to make an analysis to the separation and purification process performed this time and form an analysis report. Then it goes to step 37.

Step 331: if a matched data record is retrieved, the user will then be asked if it should be downloaded for use. If the user chooses to download, then it goes to step 35, if not, goes to step 36.

Step 35: the user purchases and downloads the matched separation and purification process, and the control module 113 goes to an automatic separation and purification process.

Step 351: the execution module 111 (the separation and purification unit) finishes separating and purifying the target compound system according to the user downloaded separation and purification process. During the process of executing the separation and purification, the user may adjust and optimize the according separation and purification factors.

Step 352: after finishing the execution, the control module 113 generates the data record of the process performed this time, and goes to step 39, while feeds the related factors back to the query and trade analysis module 114 to analysis and compare the process performed this time and the (downloaded) matched process before forming an analysis report. It goes to step 332.

Step 332: according to the analysis report of the query and trade analysis module 114, if the user has made modification, adjustment or optimization to the separation and purification factors during the execution process, then it will be decided if there is a significant improvement or enhancement on the efficiency of the process executed this time comparing to that of the matched process, if there is, then goes to step 37; otherwise, goes to step 38. If there is no modification to the downloaded process and it was performed directly, then goes to step 38.

Step 36: the control module 113 guides the user to enter the manual separation and purification step 34, 341 and 342.

Step 361: the query and trade analysis module 114 makes an analysis and comparison to the efficiency values of the process fed back by the execution module 111 performed this time and the matched existing separation and purification processes in the knowledge base 02: if comparing to the matched existing separation and purification process in the knowledge base 02, the efficiency value of the process performed this time has a significant improvement and enhancement, then the user will be prompted that he may upload this process to replace the existing process for trading; if comparing to the matched existing separation and purification process in the knowledge base 02, the efficiency value of the process performed this time has no significant improvement and enhancement, or it is even less than that of the existing process, then the analysis report will summarize and suggest the user that, next time, he should purchase and download the existing process directly next time, to achieve an effect of improving the efficiency and saving the sources.

Step 37: the query and trade analysis module 114 prompts the user that he may upload the process performed this time for trade. If the user agrees to upload, then this process will be uploaded to the knowledge base 02 for corresponding processes. If the user does not agree to upload, then this process will be saved to the local knowledge base module 112 for users within the organization to use.

Step 38: the query and trade analysis module 114 prompts the user to make an assessment to the downloaded process, while a default assessment is "effective". If the efficiency value of the real process performed this time has a pretty large deviation to the declared efficiency value of the matched process, the user may comment on the process and communicate with the publisher, so as to achieve an effect of verifying and promoting the process.

Step 39: if the chemical device or apparatus 11 has successfully performed the related chemical process of the target compound or the target compound system, including but not limited to the synthetic process and the separation and purification process, then the control module 113 will generate the supply information of the target compound and prompt the user that the organization he locates may be selected as a potential supplier which has been verified by the chemical device or apparatus 11 for the said target compound.

Figure 4:
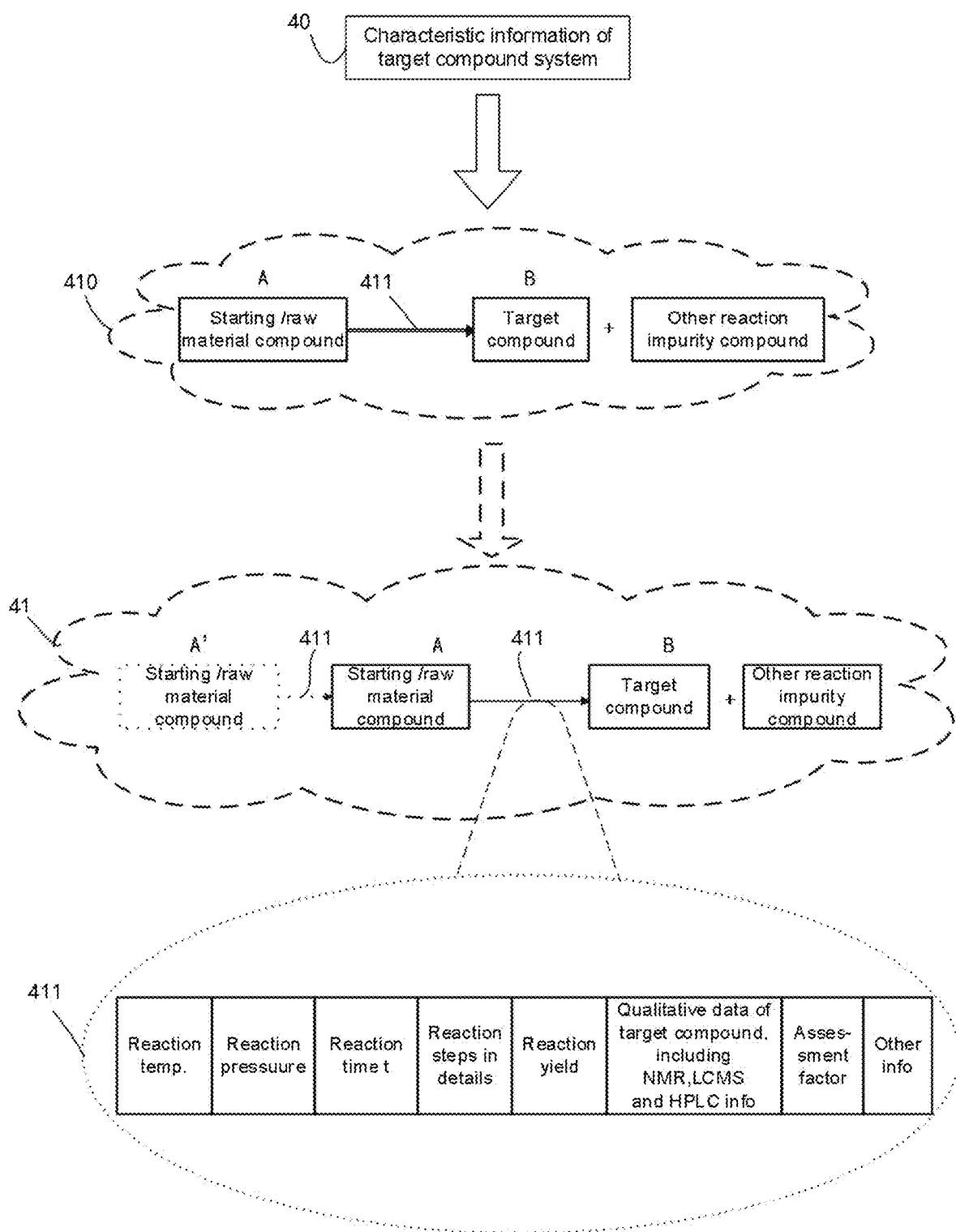
FIG. 4 illustrates a schematic diagram on obtaining one-step synthetic route information of a target compound and further obtaining whole synthetic route information of the target compound according to characteristic information of a target compound system.

As an embodiment of the present application, FIG. 4 illustrates a principle and method on obtaining one-step synthetic route information of a target compound and further obtaining whole synthetic route information of the target compound according to the characteristic information of the target compound system. Referencing to FIG. 4, the user inputs the characteristic information of the target compound system 40 through the terminal device 12 connecting to the chemical device or apparatus 11 through the network connection 14, The chemical device or apparatus 11 analyzes the one-step synthetic route information 410 of the target compound according to the obtained characteristic information 40 of the target compound system.

Further, a starting compound A may be synthesized from a starting compound A'. And so on, when the supply information of a starting compound matches a certain condition, it will be possible to decide the whole synthetic route information 41 of the target compound.

Further, the user may input and/or update a synthetic process 411 of the one-step synthetic route information 410 of the target compound on the e-business website or the APP program installed in a mobile terminal through the terminal device 12. The synthetic process 411 includes but not limited to a reaction temperature T of the synthesis, a reaction pressure P, a reaction time t, a plurality of specific operation steps or processes of the synthetic reaction, a reaction yield, a qualitative data of the target compound, an assessment factor, and other related information.

Figure 5:
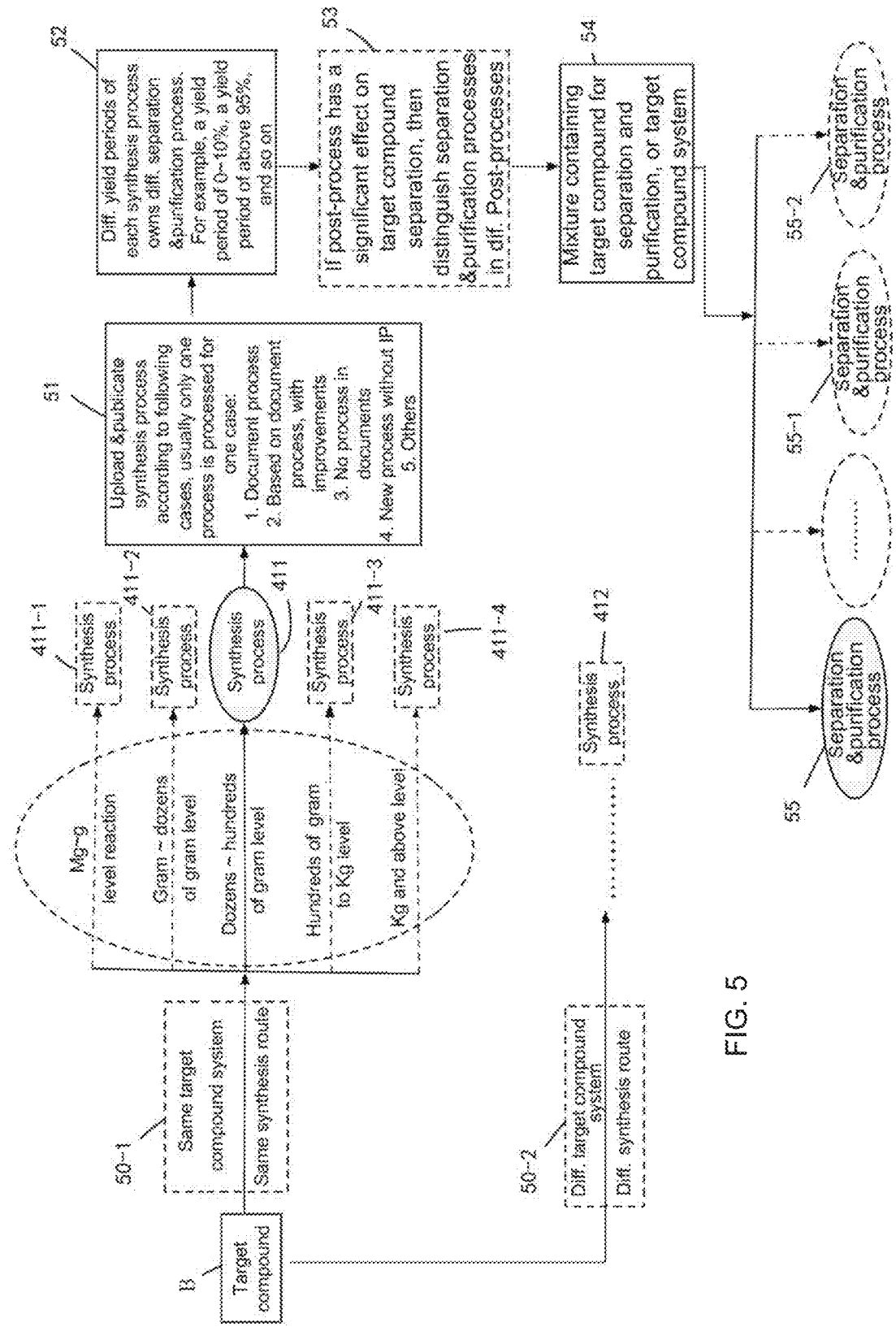
FIG. 5 illustrates a schematic diagram on distinguishing a synthetic process of a target compound and the according target compound system from the separation and purification process thereof.

As an embodiment of the present application, FIG. 5 has described a principle and method to distinguish a synthetic process of a target compound and the according target compound system from the separation and purification process thereof. The present embodiment is applied to explaining the according chemical process of the chemistry information of a target compound owns a uniqueness, which means that, the target compound or the target compound system may enumerate (distinguish) each type of the chemical process associated with the target compound or the target compound system according to a plurality of conditions including the source, the target compound yield, and the post-reaction processing treatments. The present embodiment is further applied to explaining that each type of the chemical process of each target compound and/or the target compound system has an assessed efficiency value, which is a transaction reference basis for the chemical process.

Referencing to FIG. 5, a target compound B may be synthesized by different synthetic routes (50-1, 50-2 . . . ), each synthetic route is corresponding to a different synthetic process (411, 412 . . . , and so on). Further, each synthetic route (50-1) may be further distinguished into different synthetic processes (411, 411-1, 411-2, 411-3, 411-4, and so on) due to different synthesis orders.

Step 51: each synthetic process 411 is stored in the e-business website, the App program installed in the mobile terminal and the knowledge base 02 described by the present application. According to each condition described in step 51, each of different users may upload a synthetic process 411, but for each synthetic process 411 and for all the conditions described in step 51, only the synthetic process 411 with the highest assessment factor, that is, the highest efficiency value, may be traded. Further:

Step 52: the synthetic process 411, especially the synthetic process 411 in a developing stage may generate different yields (yield periods) due to different operation levels of the user or other interference factors, while different yields (yield periods) may cause a different amount of the target compound B in the target compound system 54, thus it may affect the factor of the separation and purification process, and form different separation and purification processes (55, 55-1, 55-2 . . . , and so on). Further:

Step 53: a different post-reaction processing treatments technology may also cause a different amount of the target compound B in the target compound system 54, thus it may affect the factor of the separation and purification process, forming different separation and purification processes (55, 55-1, 55-2 . . . , and so on). Similarly, according to each condition described in steps 52, 53, different users may upload a separation and purification process 55, but only the separation and purification process 55 having the highest assessment factor, that is the highest efficiency value, may be traded.

The present application provides a user (a researcher, an actual creator and user of the chemistry information and chemical products) a platform capable of obtaining, verifying, updating and trading the chemistry information, through e-business websites having a social and trading function and the App programs installed in the mobile devices, as well as the chemical devices or apparatuses 11.

On one hand, the user may use the terminal device 12 to search the knowledge base 02 capable of obtaining the chemistry information of the target compound or the target compound system, and may obtain the related chemical process of the target compound or the target compound system through trading and using the chemical devices or apparatuses 11 to perform the chemical processes. After applying the obtained chemistry information, the user may evaluate/comment the said chemistry information and interact with the publisher of the said chemistry information, or other users using the said chemistry information through the platform described in the present invention, so as to improve the accuracy and efficiency of the said chemistry information through a plurality of methods including verifying, assessing and improving. Further, after obtaining the chemistry information of the target compound or the target compound system through trading, the user may optimize the said chemistry information by a method of referencing and improving before uploading to the said platform described in the present application to replace the existing chemistry information for trading, part of a corresponding benefit achieved from the trading may be distributed by the said platform to the publisher of the cited chemistry information, so as to guide and drive the user to publish, share and develop a higher efficiency chemistry information.

On another hand, the user may use the terminal device 12 to upload the chemistry information of the target compound or the target compound system not recorded in the knowledge base 02, and generates the corresponding chemistry information after executing the related chemical process of the target compound or the target compound system by using the chemical device or apparatus 11, before uploading to the platform described in the present application for sharing and trading.

Further, shown as the embodiment in FIG. 5, among all the related chemical process of the target compound or the target compound system recorded in the platform owning a trading function as described in the present application (including but not limited to the synthetic processes and the separation and purification processes), only the chemical process having the highest assessment factor, that is, the highest efficiency value, may be traded.

Furthermore, if the chemical process uploaded by a user has been improved by another user before being traded in the platform described in the present application, then the user being cited and/or the organization he locates may also achieve a certain ratio of the trading benefit.

Although in order to simplify an explanation, the above methods have been illustrated and described as a series of actions, it should be understood that, these methods are not limited to a sequence of the actions, since in accordance with one or more embodiments, some actions may occur in a different sequence and/or together with other actions either or not being illustrated and described in the present application, as long as they may be understood by the skilled in the art.

The skilled in the art may further realize that, each explanatory logic block, module, circuit, and algorithm step described combining the embodiments disclosed in the present application, may be achieved as an electronic hardware, computer software, or their combinations. In order to explain clearly such interchangeability between hardware and software, it was described above in general in a functional form for various explanatory component, box, module, circuit, and step. It depends on a plurality of specific implementations and design constraints imposed on the whole system that such kind of functionality shall be achieved in a hardware or software form. Skilled in the art may achieve the described functionality of each specific application in a different method, but such an implementation protocol should not be considered causing a departure from the scope of the present application.

Combining with the embodiments disclosed in the present application, various explanatory logic blocks, modules and circuits may be achieved and implemented by a general processor, a digital signal processor (DSP), an application-specific integrated circuit (ASIC), a field-programmable gate array (FPGA) or other programmable logic device, discrete gate or transistor logic, discrete hardware component, or any of their combinations designed to perform the functions described in the present application. The general processor may be a micro-processor, but in an alternative protocol, the processor may be any regular processor, controller, micro-controller, or state machine. The processor may further be achieved as a combination of computing devices, such as a combination of DSP and micro-processor, a plurality of micro-processors, one or a plurality of micro-processors cooperating with a DSP core, or any other combinations similar.

The steps of the methods or algorithm described combining with the embodiments disclosed in the present application may be achieved directly in a hardware module, a software module executed by the processor, or a combination of both. The software module may reside in a RAM memory, a flash memory, a ROM memory, an EPROM memory, an EEPROM memory, a register, a hard disk, a removable disk, a CD-ROM, or any other forms of storage media known in the art. An exemplary storage medium may be coupled to the processor such that the processor may read and write information from/to the storage medium. In an alternative protocol, the storage medium may be integrated into a processor. The processor and the storage medium may reside in the ASIC, while the ASIC may reside in the user terminal. In an alternative design, the processor and the storage medium may reside in the user terminal as a discrete component.

In one or a plurality of exemplary embodiments, the described functions may be achieved in hardware, software, a firmware or any combinations thereof. If it is achieved in software, it will be a product of computer program, then each function may be one or a plurality of instructions or codes saved in or transmitted through a computer readable medium. The computer readable medium includes a computer storage medium and a communication medium, which includes any medium allowing a computer program to transmit from one place to another. The storage medium may be any available medium being able to access by a computer. As an example instead of a restriction, such a computer readable medium may include a RAM, a ROM, an EEPROM, a CD-ROM or other optical disk storage, disk storage, or other magnetic storage device, or any other medium being able to be applied to carrying or storing any program codes in a format of instruction or data structure, and being able to be accessed by a computer. Any connection may also be formally called a computer readable medium. For example, if a software is transmitted from a website, a sever, or other remote sources through a coaxial cable, a fiber optic cable, a twisted pair cable, a digital subscriber line (DSL), or a plurality of wireless technologies such as infrared, radio, microwave and so on, then such a coaxial cable, fiber optic cable, twisted pair cable, DSL, or wireless technologies such as infrared, radio, microwave and so on will be included in a definition of medium. For example, "disk" and "disc" used in the present application include a compact disc (CD), a laser disc, an optical disc, a digital video disc (DVD), a floppy disk, and a blue light disc, wherein a "disk" usually reproduces data in a way of magnetism, while a "disc" reproduces data in an optical way using a laser. Any combinations of what described above should also be included in a range of the computer readable medium.

The foregoing description of the present disclosure is provided to enable any personnel skilled in the art to make or use the present disclosure. Various modifications to the disclosure will be apparent to those skilled in the art, and the generic principles defined herein may be applied to other variations without departing from the spirit or scope of the present disclosure. Thus, the disclosure is not intended to be limited to the embodiments and designs described herein, but should be accorded a widest scope consistent with the principles and novel features disclosed herein.

What is claimed is:

1. An apparatus for improving chemical process efficiency and promoting sharing of chemistry information, applied to obtaining and querying characteristic information and chemistry information of the target compound or the target compound system, as well as generating and/or executing a chemical process of the target compound or the target compound system, the apparatus comprises a processor further comprising an execution module, a knowledge base module, a control module and a query and trade analysis module, wherein the execution module, applied to generating and/or executing a chemical process designed by a user or obtained through an electronic transaction, of the target compound or the target compound system;

the knowledge base module, applied to storing the chemistry information of the target compound and/or the target compound system, each type of the chemical process of each target compound and/or each target compound system has an assessed efficiency value, the assessed efficiency value is a reference basis for a chemical process transaction;

the control module, applied to communicating and controlling the execution module, the knowledge base module, and the query and trade analysis module wherein the control module directs the query and trade analysis module to receive the characteristic information of the target compound or the target compound system, and search for the matched chemistry information of the target compound or the target compound system in the knowledge base module of the apparatus, and in the knowledge base module of other devices and/or the remote central database server connected into the internet through the knowledge base module of the apparatus, followed by delivering the retrieved matched chemical processes of the target compound or the target compound system to the execution module to execute the chemical process of the target compound or the target compound system;

the query and trade analysis module, further includes a matching unit, a transaction unit, and an analysis unit, wherein the matching unit, applied to searching the knowledge base module of the apparatus, a plurality of other knowledge base modules connected into a network, or a remote central database server for matched chemistry information and/or matched chemical process of the target compound and/or the target compound system through obtained characteristic information of the target compound and/or the target compound system;

the transaction unit, applied to obtaining the matched chemistry information and/or matched chemical process of the target compound and/or the target compound system through electronic transaction, initiated by the user;

the analysis unit, applied to executing an assessment and analysis to the efficiency of the executed chemical process after executing the chemical process, the chemical process is either designed by the user or obtained through electronic transaction;

wherein the user updates and/or improves the obtained matched chemical processes, after the transaction unit obtains the matched chemical process through electronic transaction according to the user's request, followed by being executed by the execution module, if the matching unit has retrieved the chemical process information matching the target compound and/or the target compound system; and after finishing performing the chemical processes updated or improved by the user, the analysis unit will evaluate the efficiency of the user updated or improved chemical process performed this time accordingly, and perform a comparison of the efficiency value based on the user updated and/or improved chemical process performed this time with the matched efficiency value of the chemical process stored in the knowledge base before generating a analysis report, followed by a plurality of according operations performed by the control module and based on an analysis and comparison result of the assessed efficiency value of the user updated and/or improved chemical process performed this time higher than the matched assessed efficiency value of the chemical process stored in the knowledge base, the user will be prompted and guided to perform an update operation to the knowledge base.

2. The apparatus for improving chemical process efficiency and promoting sharing of chemistry information according to claim 1, wherein the same type of chemical process of the same target compound and/or the target compound system is prioritized based on its assessed efficiency values in the knowledge base module, and only the chemical processes of the target compounds and/or the target compound system with the highest assessed efficiency values may be traded.

3. The apparatus for improving chemical process efficiency and promoting sharing of chemistry information according to claim 1, wherein the analysis unit evaluates accordingly the efficiency of the user designed chemical process performed this time after the user designed chemical process is executed, and generates an analysis report based on a comparison result of the efficiency value between the user designed chemical process performed this time and the matched chemical process stored in the knowledge base, if the matching unit has retrieved a matched chemical process information of the target compound and/or the target compound system, while the execution module is still executing the user designed chemical process according to the user's selection, followed by a plurality of corresponding operations executed by the control module.

4. The apparatus for improving chemical process efficiency and promoting sharing of chemistry information according to claim 1, wherein the execution unit performs the user designed chemical process, and the analysis unit performs assessment and analysis on the efficiency of the executed chemical process, before a plurality of according operations being performed by the control module, if the matching unit has not retrieved any chemical process information matching the target compound and/or the target compound system.

5. The apparatus for improving chemical process efficiency and promoting sharing of chemistry information according to claim 1, wherein an according operation of the control module is: the control module generates one-step synthetic route information of the target compound according to the characteristic information of target compound system, the one-step synthetic route information is then correlated to the chemical process of the target compound or the target compound system generated by the execution module and the supply information of the target compound obtained, before being saved to the knowledge base module, as well as prompting and guiding the user to upload the newly added or updated and/or improved chemical process of the target compound or the target compound system to the knowledge base.

6. The apparatus for improving chemical process efficiency and promoting sharing of chemistry information according to claim 1, wherein the query and trade analysis module is running in a computer chip of the apparatus or in an independent terminal device.

7. The apparatus for improving chemical process efficiency and promoting sharing of chemistry information according to claim 1, wherein the execution module comprises a separation and purification unit or a chemical synthetic reaction unit, wherein the separation and purification unit includes a chromatographic apparatus, a crystallization/re-crystallization apparatus, and a rectifying apparatus.

8. The apparatus for improving chemical process efficiency and promoting sharing of chemistry information according to claim 1, wherein the chemistry information of the target compound or the target compound system stored in the knowledge base module includes synthetic route information, separation and purification method information and supply information of the target compound, while the knowledge base module interacts with the external central database server or the knowledge base modules of other apparatuses for data obtaining and updating.

9. A method for improving chemical process efficiency and promoting sharing of chemistry information, comprising a processor that performs the steps of:

receiving the characteristic information of the target compound or the target compound system;

searching for the matched chemistry information of the target compound and/or the target compound system in the knowledge base of the apparatus, in the knowledge base of other apparatuses, and in the remote central database server locating at a far end of the Internet, according to the characteristic information of the target compound or the target compound system;

obtaining the matched chemistry information of the target compound and/or the target compound system through electronic transaction upon a user's request, wherein each type of the chemical process of each target compound or target compound system has an assessed efficiency value, and the assessed efficiency value is a reference basis for the chemical process transaction;

executing the user designed chemical process, or executing directly the chemical process obtained through the electronic transaction, or executing the user updated or improved chemical process obtained through the electronic transaction, followed by performing assessments to the efficiency of the executed chemical process after the execution finished;

based on an analysis and comparison result between the assessed efficiency value of the chemical process executed this time with the efficiency value of the matched chemical process stored in the knowledge base, prompting and guiding the user to add or update the chemistry information of the target compound or the target compound system stored in the knowledge base;

wherein the user updates and/or improves the matched chemical processes after the matched chemical process is obtained through an electronic transaction according to the user's request, if the chemical process information matching the target compound and/or the target compound system has been retrieved; the user then directs the execution module to execute the updated and/or improved chemical process, and after finishing executing the chemical processes updated or improved by the user, the efficiency of the user updated or improved chemical process performed this time will be evaluated, and based on an analysis and comparison result of the assessed efficiency value of the user updated and/or improved chemical process performed this time higher than the matched assessed efficiency value of the chemical process stored in the knowledge base, the user will be prompted and guided to perform an update operation to the knowledge base.

10. The method for improving chemical process efficiency and promoting sharing of chemistry information according to claim 9, wherein a same type of chemical process of the same target compound or target compound system stored in the knowledge base is prioritized based on its assessed efficiency value, only the chemical process of the target compound and/or the target compound system with a highest assessed efficiency value may be traded.

11. The method for improving chemical process efficiency and promoting sharing of chemistry information according to claim 9, wherein the efficiency of the user designed chemical process performed this time is assessed after executing the user designed chemical process, if a chemical process information matching the target compound or the target compound system is retrieved, while the system is still executing the user designed chemical process; and the user is prompted and guided to perform an update operation to the knowledge base, based on an analysis and comparison result of the assessed efficiency value of the user designed chemical process performed this time higher than that of the matched chemical process stored in the knowledge base.

12. The method for improving chemical process efficiency and promoting sharing of chemistry information according to claim 9, wherein the user designed chemical process will be executed, if any chemical process information matching the target compound and/or the target compound system are not retrieved, and a plurality of adding operations to the knowledge base will be performed after assessing and analyzing the efficiency of the executed chemical process.

13. The method for improving chemical process efficiency and promoting sharing of chemistry information according to claim 9, wherein the chemistry information of the target compound or the target compound system stored in the knowledge base includes the synthetic route information, the separation and purification method information and the supply information of the target compound, the knowledge base interacts with the external central database server or the knowledge base in other apparatuses for data obtaining and updating.

* * * * *